United States Patent [19]
Chapples et al.

[11] Patent Number: 5,632,875
[45] Date of Patent: May 27, 1997

[54] ELECTROCHEMICAL GAS SENSOR ASSEMBLY

[75] Inventors: John Chapples, Hants; Peter J. Sewell, Hampshire, both of Great Britain

[73] Assignee: City Technology Limited, Portsmouth, Great Britain

[21] Appl. No.: 673,727

[22] Filed: Jun. 26, 1996

[30] Foreign Application Priority Data

Aug. 29, 1995 [GB] United Kingdom ............... 9517620

[51] Int. Cl.$^6$ ................................................. G01N 27/401
[52] U.S. Cl. .......................... 204/431; 204/415; 204/432; 204/435
[58] Field of Search .................... 204/415, 435, 204/431, 432

[56] References Cited

U.S. PATENT DOCUMENTS

| | | | |
|---|---|---|---|
| 3,103,480 | 9/1963 | Watanabe | 204/435 |
| 3,329,599 | 7/1967 | Brewer | 204/413 |
| 3,855,096 | 12/1974 | Bergman | 204/415 |
| 4,310,399 | 1/1982 | Columbus | 204/435 |
| 5,395,507 | 3/1995 | Aston et al. | 204/415 |

FOREIGN PATENT DOCUMENTS

| | | |
|---|---|---|
| 0604012 | 6/1994 | European Pat. Off. . |
| 1 313 480 | 4/1973 | United Kingdom . |
| 2094005 | 9/1982 | United Kingdom . |

*Primary Examiner*—T. Tung
*Attorney, Agent, or Firm*—Lee, Mann, Smith, McWilliams, Sweeney & Ohlson

[57] ABSTRACT

An electrochemical gas sensor assembly comprises an electrochemical gas sensor; an electrolyte reservoir (3); and at least one capillary (9) defined by substantially rigid, non-porous walls for conveying electrolyte between the reservoir and the gas sensor.

16 Claims, 2 Drawing Sheets

ELECTROCHEMICAL GAS SENSOR ASSEMBLY

FIELD OF THE INVENTION

The invention relates to an electrochemical gas sensor assembly of the kind comprising an electrochemical gas sensor; an electrolyte reservoir; and means for conveying electrolyte to the gas sensor. Such electrochemical gas sensor assemblies are hereinafter referred to as of the kind described.

DESCRIPTION OF THE PRIOR ART

An example of an electrochemical gas sensor assembly of the kind described is shown in GB-A-2094005. In this case, the reservoir is provided in a hollowed out bottom plate which has a covering flange which supports the various components of the sensor including the sensing and counter electrodes and, where provided, a reference electrode. Electrolyte passes through a small aperture in the covering flange in a wick extending into the reservoir and extending through apertures in some of the components and into contact with hydrophilic separators to convey electrolyte to the region between the electrodes. The use of a wick is undesirable due to the complex manufacturing techniques required to thread the wick through the various components. Furthermore, the arrangement requires an additional rear vent which provides a possible source of leakage as well as leading to a more complex construction.

More recently, it has been proposed to provide the conveying means as a porous, block-like body positioned in the reservoir and at least partly supporting other components of the sensor. This is described in more detail in EP-A-0604012. Although this approach leads to a simpler assembly and the ability to pre-fill the reservoir, it has the disadvantages of relatively high cost and some difficulties in assembly because the block-like body tends to float in the electrolyte. In some cases, the tolerances achievable with materials for the block such as Reticulated Vitreous Carbon (RVC) are not compatible with the manufacturing tolerances required and there is also a risk of contamination when the block-like body is cut.

SUMMARY OF THE INVENTION

In accordance with the present invention, an electrochemical gas sensor of the kind described is provided with conveying means in the form of at least one capillary defined by substantially rigid, non-porous walls for conveying electrolyte between the reservoir and the gas sensor.

We have devised a new form of conveying means which is defined by a substantially rigid, non-porous component or components and which thus overcomes the problems of conventional conveying means as set out above. In view of the substantially rigid nature of the walls, it is possible to manufacture the walls to very close and accurate tolerances and also maximise space within the reservoir by minimising the wall thickness.

In some cases, the capillary walls may be defined by an integral part of the reservoir, for example the reservoir could be made from moulded plastics and include the at least one capillary. However, in general this will be difficult to achieve and preferably the capillary walls are defined by cooperating parts of the reservoir and a substantially rigid, non-porous body. Conveniently, the body is removable from the reservoir although this is not essential.

There are various ways in which the walls of the capillary could be defined but conveniently, where a substantially rigid, non-porous body is provided, the reservoir includes an upstanding wall, the body having an aperture into which the upstanding wall is positioned so that the at least one capillary is defined between the upstanding wall and the body. Not only does this provide a very convenient way of defining the or each capillary but in addition the upstanding wall assists in locating the body within the reservoir which is useful both during assembly and in use. In an alternative, the at least one capillary could be defined between the body and an outer wall of the reservoir.

In some cases, the capillary could have an annular form extending around the upstanding wall and carrying electrolyte along the upstanding wall but preferably the reservoir includes a number of upstanding walls each extending into the aperture of the body to define respective capillaries. Conveniently, one or both of the or each upstanding wall and the body aperture have ribs which extend between the body and the respective upstanding walls so as to define the lateral extent of the or each capillary. In this way, it will be possible to define more than one capillary extending along the length of the or each upstanding wall.

The or each capillary could simply extend along the length of the or each upstanding wall. This would be acceptable if the sensor was used in a single orientation in which electrolyte was encouraged to flow to the base of the upstanding wall where it could be received in the capillary. In practice, however, the orientation of the sensor will vary during use and preferably, therefore, part of the at least one capillary is defined between the body and a base of the reservoir. In this way, electrolyte can be obtained from parts of the base spaced from the upstanding wall and then conveyed by that part of the capillary defined between the body and the base to the upstanding wall(s) for onward transport to the gas sensor.

The part of the body which cooperates with the base could take a variety of forms, for example the body could include one or more laterally extending arms but conveniently the body has a first flange extending across the base but spaced therefrom to define the part of the at least one capillary. Preferably, in this case, one or both of the base and the first flange have a number of ribs which extend between the base and the flange to define the part of the at least one capillary.

Preferably the body has a second flange positioned adjacent the gas sensor so as partly to support the gas sensor. In some cases, during use or transport, the sensor assembly could be reoriented and thus preferably one or both of the second flange and facing surface of the gas sensor have a number of ribs which extend therebetween to define one or more capillaries for conveying electrolyte.

It is important to minimise the volume taken up by the body within the reservoir. This can be achieved by minimising the thickness of the various walls within the reservoir but in addition preferably the first and/or second flanges has one or more apertures extending therethrough. Providing apertures in the second flange also assists in filling the reservoir during assembly and wetting the adjacent gas sensor surface.

In some conventional sensor assemblies as described above, it is necessary to provide a rear, air vent to allow air to be displaced as the reservoir fills and to allow entry of air as the reservoir empties due to water transfer in response to humidity changes. In the present case, a rear air vent is not essential and conveniently the second flange is spaced from the reservoir wall to define an air vent.

The gas sensor can be of any conventional construction and will typically comprise sensing, counter and optionally reference electrodes and means for conveying electrolyte from the at least one capillary to between the sensing and counter electrodes.

BRIEF DESCRIPTION OF THE DRAWINGS

An example of an electrochemical gas sensor assembly according to the invention will now be described with reference to the accompanying drawings, in which.

DETAILED DESCRIPTION OF THE EMBODIMENT

Figure 1:
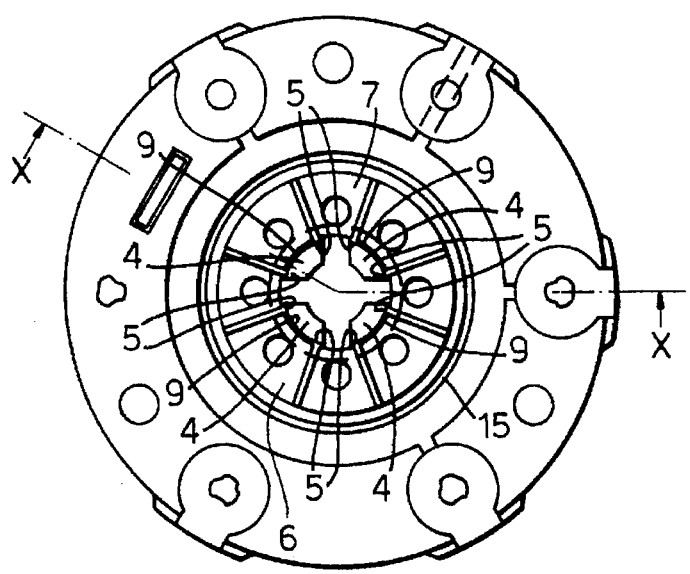
FIG. 1 is a plan of the reservoir of the assembly.
Figure 2:
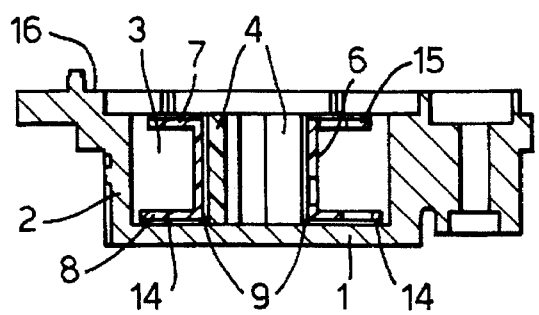
FIG. 2 is a section taken along the line X—X in FIG. 1.

The reservoir shown in FIGS. 1 and 2, which is to be fitted to a gas sensor, includes a base 1 (FIG. 2) integrally moulded with an upstanding, annular outer wall 2 defining an electrolyte cavity 3. A set of four integrally moulded, circumferentially spaced, upstanding walls 4 extend from the centre of the base 1.

An annular sleeve 6 having upper and lower flanges 7,8 integrally formed therewith fits onto the walls 4 as can be seen most clearly in FIG. 2. The sleeve 6 is a close fit on the walls 4 so as to define four elongate capillaries 9. The sleeve 6 has four pairs of ribs 5 which extend parallel with the walls 4 to define the lateral extent of each capillary 9. The radial width of each capillary 9 is about 0.2 mm.

Figure 4:
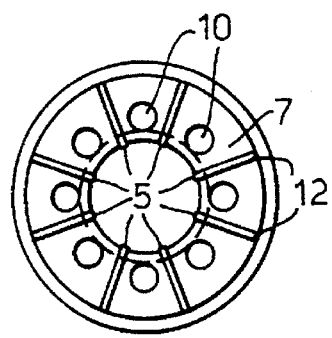
FIG. 4 is a plan of the body shown in FIG. 3.
Figure 3:
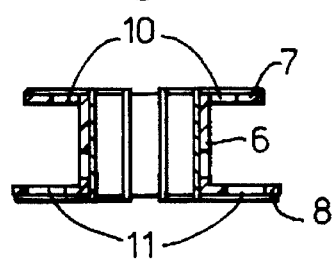
FIG. 3 is a cross-section through the non-porous body of the reservoir shown in FIGS. 1 and 2.
Figure 5:
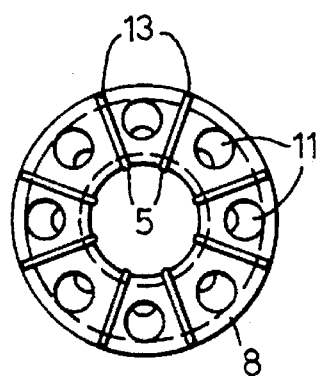
FIG. 5 is a bottom plan of the body shown in FIG. 3.

Each of the upper and lower flanges 7,8 is formed with a number of circumferentially spaced apertures 10,11 respectively (FIGS. 3–5) and is also formed with a set of substantially equally circumferentially spaced and axially outward facing ribs 12,13 respectively which are aligned with the ribs 5.

The ribs 13 on the flange 8 cooperate with the base 1 of the reservoir to define a number of radially extending capillaries 14 between each pair of ribs, these capillaries having a height (as seen in FIG. 2) of between 0.2 and 0.3 mm. A similar set of capillaries is formed between the ribs 12 and the lowermost part of the gas sensor (as shown in FIGS. 1–5).

The apertures 10,11 are provided for a number of reasons. Firstly, they reduce the volume taken up by the flanges 7,8. The apertures 10, however, also facilitate filling of the reservoir which can be achieved through the apertures 10 and also assist in wetting the adjacent surface of the gas sensor.

It will be noted in FIGS. 1 and 2 that the upper flange 7 has a radius less than that of the inner surface of the wall 2 so as to define an annular gap 15. This provides an air vent as will be described below.

The material of the walls 4 and the sleeve 6 is non-porous and substantially rigid and conveniently is formed of a plastics material such as ABS or polycarbonate. In general, any thermoplastic will be suitable which is compatible with the electrolyte to be used.

Figure 6:
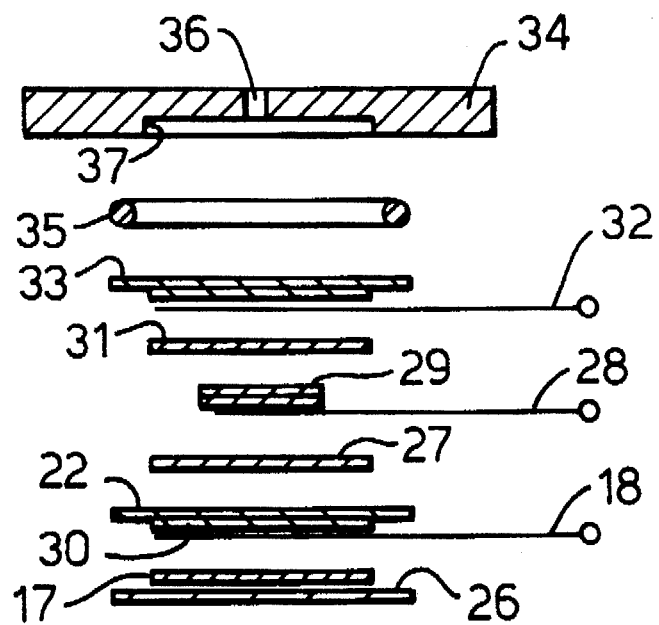
FIG. 6 is an exploded section through the gas sensor which is mounted on the reservoir shown in FIG. 1.

During manufacture, the base and wall 1,2 of the reservoir and the walls 4 are formed as an integral, moulded part which is assembled with a moulded body defining the sleeve 6 and flanges 7,8. Electrolyte is then supplied to the reservoir (typically about 1 cc) and then the gas sensor is assembled on top of the reservoir and secured to it. The components of the gas sensor can take a variety of forms, one example of which is shown in FIG. 6. Positioned immediately above the flange 7 and partially supported by the flange and partly by a ledge 16 of the wall 2 are positioned a PTFE tape floor seal 26, a hydrophilic separator 17, a current collector 18 and a counter electrode 22. A separator 27 of hydrophilic material is positioned above the counter electrode 22 followed by a current collector 28, a reference electrode 29, a separator 31, a current collector 32 and a sensing electrode 33. Each of the electrodes is provided on PTFE backing tape. The components are held in place by sealing a top plate 34 onto the reservoir, the various components being urged into contact by an "O"-ring 35. The top plate 34 has a capillary hole 36 which forms a gas phase diffusion barrier for restricting access of the gas to be detected, the top plate also having a cavity 37 to allow for lateral diffusion of the gas across the sensing electrode 33. As an alternative to the gas phase diffusion barrier, a Knudsen barrier or solid membrane could be used.

It should be understood that this is just one example of components for a suitable gas sensor and there are many other forms known in the art which would also be suitable for use with the reservoir shown in FIGS. 1 and 2.

Initially, after all the components have been assembled together the electrolyte will not automatically wet the sensor components. The sensor is therefore inverted to cause the electrolyte in the reservoir to prime or wet the sensor components through the holes 10 which will then draw electrolyte through the capillaries 9. During use, in drying conditions, if the electrolyte loses water, further electrolyte is drawn up through the capillaries 14 and then 9 and is fed through an aperture 30 in the counter electrode 22 and into the region between the electrodes. During this action, air can enter the reservoir through the PTFE backing tapes and through the air vent 15. Under humid conditions, the reverse action will take place with liquid being drawn back through the capillaries into the reservoir. In this case, air is displaced out of the reservoir through the air vent 15 and across the PTFE backing tapes and out to the atmosphere.

It will be noted that this construction for the reservoir enables the size and shape of the capillaries to be very accurately defined and, in contrast to conventional arrangements, these capillaries will maintain their form during use because of the rigid nature of the components defining capillaries. In addition, the upper flange 7 provides strong, rigid support for the gas sensor components. It should be noted, however, that the upper flange 7 (and lower flange 8) need not have an annular form but could be formed by one or more radially extending arms.

We claim:

1. An electrochemical gas sensor assembly comprising an electrochemical gas sensor having sensing and counter electrodes; an electrolyte reservoir; and at least one capillary defined by substantially rigid, non-porous walls for conveying electrolyte between said reservoir and said gas sensor, wherein said reservoir includes an upstanding wall, said sensor further including a substantially rigid non-porous body having an aperture into which said upstanding wall is positioned so that said at least one capillary is defined between the upstanding wall and the body.

2. A sensor assembly according to claim 1, wherein said reservoir includes a number of upstanding walls each extending into said aperture of said body to define respective capillaries.

3. A sensor assembly according to claim 2, wherein said upstanding walls are circumferentially spaced apart.

4. A sensor assembly according to claim 1, wherein one or both of said upstanding wall and said body aperture have ribs which extend between said body and said respective upstanding walls so as to define the lateral extent of the or each capillary.

5. A sensor assembly according to claim 1, wherein said body is removable from said reservoir.

6. A sensor assembly according to claim 1, wherein part of said at least one capillary is defined between said body and a base of said reservoir.

7. A sensor assembly according to claim 6, wherein said body has a first flange extending across said base but spaced therefrom to define said part of said at least one capillary.

8. A sensor assembly according to claim 7, wherein one or both of said base and said first flange have a number of ribs which extend between said base and said flange to define the part of the at least one capillary.

9. A sensor assembly according to claim 7, wherein said body has a second flange positioned adjacent said gas sensor so as partly to support said gas sensor.

10. A sensor according to claim 9, wherein said second flange supports a facing surface defined by said gas sensor, and wherein one or both of said second flange and said facing surface of said gas sensor have a number of ribs which extend therebetween to define one or more capillaries for conveying electrolyte.

11. A sensor assembly according to claim 9, wherein said second flange is spaced from the reservoir wall to define an air vent.

12. A sensor assembly according to claim 9, wherein said second flange has one or more apertures extending therethrough.

13. A sensor assembly according to claim 7, wherein said first flange has one or more apertures extending therethrough.

14. A sensor assembly according to claim 1, wherein said body is made of a plastics material.

15. A sensor assembly according to claim 1, further comprising means for conveying electrolyte from the at least one capillary to between the sensing and counter electrodes.

16. A sensor assembly according to claim 15, wherein said gas sensor further comprises a reference electrode.

* * * * *